United States Patent [19]

Majima

[11] Patent Number: 5,766,976

[45] Date of Patent: Jun. 16, 1998

[54] METHOD FOR DETECTING CRYSTAL DEFECTS IN A SILICON SINGLE CRYSTAL SUBSTRATE

[75] Inventor: Masaki Majima, Annaka, Japan

[73] Assignee: Shin-Etsu Handotai Co., Ltd., Tokyo, Japan

[21] Appl. No.: 827,103

[22] Filed: Mar. 17, 1997

[30] Foreign Application Priority Data

Mar. 22, 1996 [JP] Japan ................................. 8-093618

[51] Int. Cl.⁶ .................................................. H01L 21/00
[52] U.S. Cl. ................................. 438/8; 216/84; 438/14
[58] Field of Search ........................... 252/79.5; 438/8, 438/16, 14, 753; 216/84, 85

[56] References Cited

U.S. PATENT DOCUMENTS 5,223,443  6/1993  Chinn et al. ................................. 438/14
5,382,551  1/1995  Thakur et al. ................................. 438/8

*Primary Examiner*—William Powell
*Attorney, Agent, or Firm*—Ronald R. Snider

[57] ABSTRACT

This invention relates to a method for detecting crystal defects in a silicon single crystal substrate which contains a dopant with the concentration of at least $7.0\times10^{16}$ atoms/$cm^3$. In the method, a native oxide film 2 on the surface of a silicon single crystal substrate 1 is removed, then copper 4 is deposited on the surface of silicon single crystal substrate 1, then the silicon single crystal substrate 1 is etched by an alkaline aqueous solution. Finally, the etched surface of silicon single crystal substrate 1 is observed by visual observation or by an optical microscope to evaluate crystal defects 3 of silicon single crystal substrate 1.

6 Claims, 2 Drawing Sheets

METHOD FOR DETECTING CRYSTAL DEFECTS IN A SILICON SINGLE CRYSTAL SUBSTRATE

RELATED APPLICATION

This application claims the priority of Japanese Patent application No. 8-93618 filed on Mar. 22, 1996, which is incorporated herein by reference.

BACKGROUND OF THE INVENTION

1. Field of the Invention

This invention relates to a method for detecting crystal defects in a silicon single crystal substrate for manufacturing a semiconductor device.

2. The Prior Art

One of methods for detecting crystal defects generated in a silicon single crystal substrate includes the step of etching a silicon substrate made from the silicon single crystal ingot by using an etching solution composed of hydrofluoric acid, nitric acid, acetic acid and water or an etching solution composed of hydrofluoric acid, chromic acid and water. This method is regarded as the simplest, quickest and most cost efficient method.

By etching the silicon substrate with the etching solution, so-called selective or preferential etching occurs wherein the etching rate is different between areas where there exist crystal defects and areas where there exist no crystal defects. Therefore, crystal defects can be detected by visual or optical microscopic observation of the surface of the selectively etched surface.

However, in the case of a silicon single crystal which contains arsenic or antimony in a high concentration, at least $7.0 \times 10^{16}$ atoms/cm$^3$, the etching rate is slower compared with the case when the dopant concentration is lower, and differences between the etching rate in areas where there exist crystal defects and areas where there exist no crystal defects. In such a case, the selective etching does not allow the observation of crystal defects.

For detecting crystal defects of the aforementioned silicon single crystals, the following methods have been used:

(1) a method in which X-ray topographic images are taken;

(2) a method which uses a transmission electron microscope for observation; and (3) a method in which epitaxial growth is conducted on the substrate, crystal defects in the substrate are introduced into the epitaxial layer, the aforementioned selective etching is conducted and then the etched epitaxial layer surface is observed.

However, these methods have a problem in that they require an X-ray generator, an electron beam generator or an epitaxial growth device. Therefore these method are neither simple nor quick in getting results. They are expensive as well.

BRIEF SUMMARY OF THE INVENTION

The object of the present invention is to provide a simple, quick and low cost method for detecting crystal defects in a silicon single crystal substrate.

The invention according to the present invention provides a method for detecting crystal defects in a silicon single crystal substrate, comprising the steps of: removing a native oxide film generated on the surface of the silicon single crystal substrate; depositing copper on the surface of the silicon single crystal substrate; etching the silicon single crystal substrate by an alkaline aqueous solution; and observing the etched surface of the silicon single crystal substrate by means of visual observation or an optical microscope.

The dopant of the silicon single crystal substrate may be selected from arsenic and antimony.

The concentration of the dopant may be at least $7.0 \times 10^{16}$ atoms/cm$^3$.

The copper depositing step may be selected from coating an aqueous solution containing copper ions on the surface of the silicon single crystal substrate and dipping the silicon single crystal substrate in an aqueous solution containing copper ions.

The copper concentration in the aqueous solution containing copper ions may be 5 ppm–2,000 ppm.

Light irradiation may be conducted in the copper depositing step.

The etching step uses an aqueous solution of sodium hydroxide or an aqueous solution of potassium hydroxide with a concentration of 0.01–2.5 mole/liter at a temperature of 5°–95° C.

BRIEF DESCRIPTION OF THE DRAWING

FIG. 1A shows the silicon substrate on the surface of which the native oxide film is formed;

FIG. 1B shows the silicon substrate after the removal of the native oxide film;

FIG. 1C shows the silicon substrate on the surface of which copper is deposited; and FIG. 1D is a section view of the silicon substrate after the etching step using the alkali aqueous solution.

EMBODIMENTS

Embodiments of the present invention are described below.

Figure 1A:
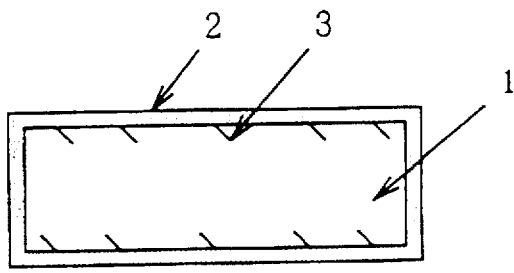
FIGS. 1A–1D are section views showing a crystal defect detection process according to the present invention, in more detail.

First, a silicon single crystal substrate 1 is prepared from a part of an ingot which has been pulled according to the Czochralski method. The silicon single crystal substrate 1 may be made according to a prior art method. The silicon single crystal substrate 1 should be free from mechanical damage due to mechanical treatment such as slicing at least in the region between the surface and a depth of several micrometers, so that a substrate, treated with a chemical etching by an etchant having substantially no selectivity for crystal defect but not yet treated with the mirror polishing process, is preferably used, however, a substrate which has been through the mirror polishing process may be also used. On the silicon single crystal substrate 1, there is usually generated a native oxide film 2, and there are crystal defects 3, as shown in FIG. 1A.

Figure 1B:
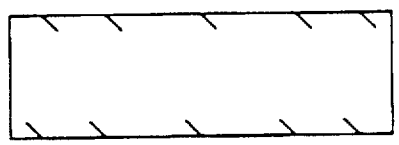

The silicon single crystal substrate 1 is then dipped in an aqueous solution which contains hydrofluoric acid to remove the native oxide film 2 formed on its surface, as shown in FIG. 1B. The concentration of the aqueous solution of hydrofluoric acid and the dipping time may be determined according to desired conditions. The removal of native oxide film 2 can be verified by observing the surface of silicon single crystal substrate 1 which becomes hydrophobic after being dipped in the aqueous solution of hydrofluoric acid if there is no native oxide on the surface.

Figure 1C:
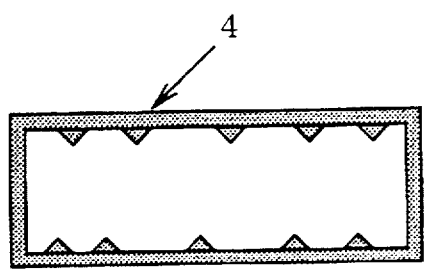

Copper 4 is then deposited on the surface of the silicon single crystal substrate 1 from which the native oxide film has been removed, either by coating an aqueous solution containing copper ions on the surface of the silicon single crystal substrate 1 or dipping the silicon single crystal substrate 1 in an aqueous solution containing copper ions. light may be irradiated using a halogen lamp and such to accelerate the deposition of copper on silicon single crystal substrate 1 when coating the aqueous solution containing copper ions on it or dipping it in the solution. The deposited copper diffuses from the surface toward the inside of silicon single crystal substrate 1. The copper tends to accumulate more and penetrates deeper to form a precipitate in areas where crystal defects exist, as shown in FIG. 1C.

The preferable concentration of the copper ion in the aqueous solution may be 5–2,000 ppm. If the concentration is below the lower limit, then the deposition of copper takes a long time, resulting in an inefficient practice. If the concentration is above the upper limit, then a large amount of copper will be deposited and dealing with it will be difficult, and this would not be economical since a large amount of copper nitrate and such would be required to prepare the aqueous solution containing copper ions.

Figure 1D:
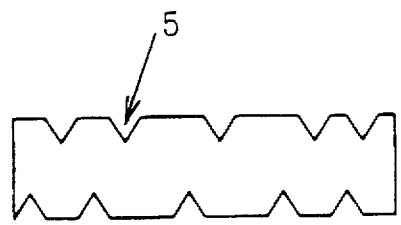

Then the substrate on which copper has been deposited is dipped in an aqueous solution of sodium hydroxide or potassium hydroxide, for example. Since this separates the copper deposited on the surface of the substrate from the surface, the surface of the silicon substrate is exposed and etched. The etching proceeds faster in crystal defect areas where the copper precipitate is formed, and therefore after the etching they can be observed as etch pits 5 by means of an optical microscope, as shown in FIG. 1D.

The concentration and the temperature of the aforementioned aqueous solution of sodium hydroxide or potassium hydroxide may be 0.01–2.5 mole/liter and 5°–95 ° C., respectively. If the temperature and/or the concentration is lower than the lower limit, then the etching of the surface of the substrate will take a long time, resulting in an inefficient practice. If it is higher than the upper limit, then etching will be too fast, making it hard to observe the crystal defects.

By carrying out the aforementioned processes, crystal defects of a silicon single crystal can be detected. Particularly in the case of a silicon single crystal substrate containing as a dopant a high concentration, at least $7.0 \times 10^{16}$ atoms/cm$^3$, of arsenic or antimony, the aforementioned simple, fast and low cost technique allows the detection of crystal defects without using an expensive and time consuming apparatus such as an X-ray generator, electron beam generator or epitaxial apparatus which used to be required.

EXAMPLES

Examples of the present invention are described below.

(Example 1)

Figure 2:
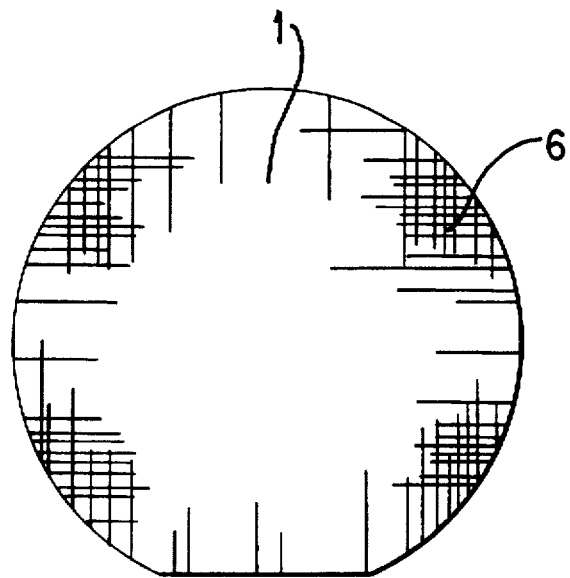
FIG. 2 shows an example wherein slip dislocations are observed by visual observation of the whole surface of the silicon substrate under a collimated light.
Figure 3:
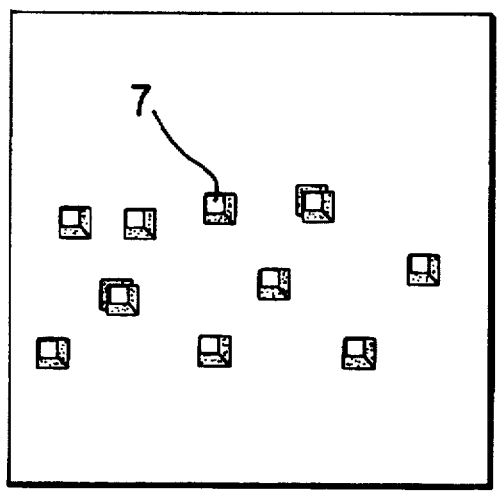
FIG. 3 shows an example of an area with slip dislocations shown in FIG. 2 magnified by an optical microscope.

A substrate with a diameter of 150 mm and a thickness of 650 micrometers which had been treated with chemical etching by an etchant having substantially no selectivity for crystal defect was prepared from a silicon single crystal ingot prepared with the Czochralski method. This ingot had a crystal plane orientation of (100), was doped with $2.0 \times 10^{19}$ atoms/cm$^3$ arsenic and had crystal defects (slip dislocations). This substrate was dipped in a 25% hydrofluoric acid aqueous solution for 5 minutes to remove the native oxide film on the surface. It was then dipped in a mixed aqueous solution of copper nitrate and hydrofluoric acid with a copper ion concentration of 100 ppm (the temperature of the aqueous solution was 23° C.) and held for 10 minutes while being irradiated by light from a halogen lamp to deposit copper on the substrate surface. This substrate on which copper had been deposited was then dipped in an aqueous solution of 0.089 mole/liter sodium hydroxide for one hour (the temperature of the aqueous solution was 23° C.). The silicon substrate was etched approximately 0.7 micrometers from the surface, and it was possible to observe areas with slip dislocations as etch pits by visual observation under a collimated light or by optical microscopic observation. FIG. 2 shows a top view of the slip dislocations observed by visual observation under a collimated light, and FIG. 3 shows a top view of the slip dislocations (etch pits) observed by optical microscopic observation.

(Example 2)

Example 2 was carried out in the same manner as Example 1 except for the fact that a silicon substrate with slip dislocations prepared from a silicon single crystal ingot with a crystal plane orientation of (111) doped with $7.0 \times 10^{18}$ atoms/cm$^3$ antimony was used. The silicon single crystal substrate was etched approximately 0.13 micrometers from the surface. It was possible to observe areas with slip dislocations as etch pits by optical microscopic observation or visual observation under a collimated light.

(Example 3)

Example 3 was carried out in the same manner as Example 1 except for the fact that the concentration of the sodium hydroxide aqueous solution was 1.0 mole/liter. The silicon single crystal substrate was etched approximately 0.9 micrometers from the surface. It was possible to observe areas with slip dislocations as etch pits by optical microscopic observation or visual observation under a collimated light.

(Example 4)

Example 4 was carried out in the same manner as Example 1 except for the fact that a 0.1 mole/liter potassium hydroxide aqueous solution was used for the alkaline aqueous solution. The silicon single crystal substrate was etched approximately 1.7 micrometers from the surface. It was possible to observe areas with slip dislocations as etch pits by optical microscopic observation or visual observation under a collimated light.

(Comparative example 1)

Comparative example 1 was carried out in the same manner as Example 1 except for the fact that the concentration of the sodium hydroxide aqueous solution was 2.6 mole/liter. The silicon single crystal substrate was etched approximately 3 micrometers from the surface. It was possible to observe areas with slip dislocations as etch pits, but they were not clear.

The examples described above targeted slip dislocations as crystal defects, but it was also verified that the detection method of the present invention was applicable for point defects such as lattice vacancy, interstitial oxygen and oxide precipitates as well as secondary defects caused by them.

What is claimed is:

1. A method for detecting crystal defects in a silicon single crystal substrate, comprising the steps of:

removing a native oxide film generated on the surface of the silicon single crystal substrate;

depositing copper on the surface of said silicon single crystal substrate;

etching said silicon single crystal substrate by an alkaline aqueous solution; and observing the etched surface of said silicon single crystal substrate by means of visual observation or an optical microscope.

2. The method for detecting crystal defects of claim 1 wherein:

the dopant of said silicon single crystal substrate is selected from arsenic and antimony; and the concentration of the dopant is selected to be at least $7.0 \times 10^{16}$ atoms/cm$^3$.

3. The method for detecting crystal defects of claim 1 wherein:

said copper depositing step is the step selected from coating an aqueous solution containing copper ions on the surface of said silicon single crystal substrate and dipping said silicon single crystal substrate in an aqueous solution containing copper ions.

4. The method for detecting crystal defects of claim 3 wherein:

the copper concentration in said aqueous solution containing copper ions is 5 ppm–2,000 ppm.

5. The method for detecting crystal defects of claim 1 wherein:

light irradiation is conducted in said copper depositing step.

6. The method for detecting crystal defects of claim 1 wherein:

said etching step uses an aqueous solution of sodium hydroxide or an aqueous solution of potassium hydroxide with a concentration of 0.01–2.5 mole/liter at a temperature of 5°–95° C.

* * * * *